United States Patent
Fetner et al.

(10) Patent No.: US 10,383,944 B2
(45) Date of Patent: Aug. 20, 2019

(54) DISPERSION COMPRISING AN ESTERIFIED CELLULOSE ETHER

(71) Applicant: Dow Global Technologies LLC, Midland, MI (US)

(72) Inventors: Neal J. Fetner, Midland, MI (US); David L. Malotky, Midland, MI (US); Jin Zhao, Midland, MI (US); Matthias Knarr, Nienburg/Weser (DE); Michael J. Devon, Midland, MI (US); Roland Adden, Bomlitz (DE)

(73) Assignee: DOW GLOBAL TECHNOLOGIES LLC, Midland, MI (US)

( * ) Notice: Subject to any disclaimer, the term of this patent is extended or adjusted under 35 U.S.C. 154(b) by 0 days.

(21) Appl. No.: 15/129,505

(22) PCT Filed: Mar. 3, 2015

(86) PCT No.: PCT/US2015/018390
§ 371 (c)(1),
(2) Date: Sep. 27, 2016

(87) PCT Pub. No.: WO2015/156922
PCT Pub. Date: Oct. 15, 2015

(65) Prior Publication Data
US 2017/0173159 A1 Jun. 22, 2017

Related U.S. Application Data

(60) Provisional application No. 62/030,751, filed on Jul. 30, 2014, provisional application No. 61/976,726, filed on Apr. 8, 2014.

(51) Int. Cl.
| | |
|---|---|
| *A61K 9/28* | (2006.01) |
| *A61K 47/38* | (2006.01) |
| *A61K 9/48* | (2006.01) |
| *C08B 13/00* | (2006.01) |
| *C08L 1/32* | (2006.01) |
| *A61J 3/07* | (2006.01) |

(52) U.S. Cl.
CPC .......... *A61K 47/38* (2013.01); *A61J 3/07* (2013.01); *A61K 9/2866* (2013.01); *A61K 9/4816* (2013.01); *C08B 13/00* (2013.01); *C08L 1/32* (2013.01)

(58) Field of Classification Search
None
See application file for complete search history.

(56) References Cited

U.S. PATENT DOCUMENTS

| | | | |
|---|---|---|---|
| 4,226,981 A | 10/1980 | Onda et al. | |
| 4,365,060 A | 12/1982 | Onda et al. | |
| 5,025,004 A | 6/1991 | Wu et al. | |
| 5,539,021 A | 7/1996 | Pate et al. | |
| 5,733,575 A * | 3/1998 | Mehra | A61K 9/2813 424/440 |
| 6,299,896 B1 * | 10/2001 | Cooper | A23L 33/15 424/400 |
| 7,138,143 B1 | 11/2006 | Mukai et al. | |
| 2004/0213847 A1 * | 10/2004 | Matharu | A61K 9/2013 424/471 |
| 2013/0012535 A1 * | 1/2013 | Kanamaru | A61K 31/403 514/301 |
| 2013/0295188 A1 | 11/2013 | Cade et al. | |

FOREIGN PATENT DOCUMENTS

| | | | |
|---|---|---|---|
| EP | 0648487 | * 4/1995 | .............. A61K 9/36 |
| EP | 0648487 A1 | 4/1995 | |
| EP | 0662323 A1 | 7/1995 | |
| EP | 0677322 B1 | 3/2001 | |
| GB | 2353215 A | 2/2001 | |
| JP | S59-190925 | 10/1984 | |
| JP | 7070203 | 3/1995 | |
| JP | 8109124 A | 4/1996 | |
| WO | 8000659 A1 | 4/1980 | |
| WO | 2008122993 A1 | 10/2008 | |
| WO | 2013164121 A1 | 11/2013 | |
| WO | 2013164122 A1 | 11/2013 | |

* cited by examiner

*Primary Examiner* — Brian Gulledge
(74) *Attorney, Agent, or Firm* — Ballard Spahr LLP

(57) ABSTRACT

An aqueous composition useful for producing capsules shells comprises a) at least one dispersed esterified cellulose ether comprising (i) groups of the formula —C(O)—R—COOA or (ii) a combination of aliphatic monovalent acyl groups and groups of the formula —C(O)—R—COOA, wherein R is a divalent aliphatic or aromatic hydrocarbon group and A is hydrogen or a cation, and b) from 0.05 to 20 percent of at least one salt of a fatty acid, based on the weight of the dispersed esterified cellulose ether, wherein the median particle size, d50, of the dispersed esterified cellulose ether particles is up to 7 micrometers, such median particle size (d50) being the size at which 50 mass percent of the particles have a smaller equivalent diameter and 50 mass percent have a larger equivalent diameter.

14 Claims, 2 Drawing Sheets

DISPERSION COMPRISING AN ESTERIFIED CELLULOSE ETHER

FIELD

This invention concerns aqueous compositions comprising dispersed esterified cellulose ethers, processes for producing the compositions, and coated dosage forms and capsule shells made from the aqueous compositions.

INTRODUCTION

Esters of cellulose ethers, their uses and processes for preparing them are generally known in the art. Known methods of producing cellulose ether-esters include the reaction of a cellulose ether with an aliphatic monocarboxylic acid anhydride or a dicarboxylic acid anhydride or a combination thereof, for example as described in U.S. Pat. Nos. 4,226,981 and 4,365,060.

Various known esterified cellulose ethers are useful as enteric polymers for pharmaceutical dosage forms, such as methylcellulose phthalate (MCP), hydroxypropyl methylcellulose phthalate (HPMCP), methylcellulose succinate (MCS), or hydroxypropyl methylcellulose acetate succinate (HPMCAS). The esterified cellulose ethers are used for coating dosage forms, such as tablets, microparticulates or capsules. Enteric polymers protect the drug from inactivation or degradation in the acidic environment or prevent irritation of the stomach by the drug, but are dissolved in the intestinal canals to release the drug contained therein. U.S. Pat. No. 4,365,060 discloses enterosoluble capsules which are said to have excellent enterosolubility behavior.

Enteric coatings or capsules can be prepared from organic or aqueous solutions of esterified cellulose ethers. European Patent Applications EP 0 662 323 and EP 0 677 322 disclose methods of preparing an aqueous emulsion for coating solid pharmaceutical preparations wherein a cellulosic polymer is dissolved in an organic solvent miscible with water or in a mixture of the organic solvent with water to give a polymer solution having a polymer concentration of not more than 10 wt. %, the solution is mixed with (additional) water to disperse the solution in water, and then organic solvent is removed. The published Japanese Patent Application JP8109124-A discloses the production of coating powders from such emulsions by adding an anionic surfactant and spray-drying. However, organic solvents are often not desirable for pharmaceutical or nutritional uses. On the other hand, esterified cellulose ethers only have a limited solubility in water. European Patent Application EP 0 648 487 discloses an aqueous dispersion comprising 5 to 15 wt. % of an enteric coating base, such as HPMCAS or HPMCP. The aqueous dispersion further comprises 15-40 wt. % of a plasticizer, such as triethyl citrate or triacetin, and 0.1-10 wt. % of an anionic surfactant, such as sodium alkyl sulfate, or a sodium or potassium salt of a fatty acid, such as sodium oleate or potassium sorbate, based on the weight of HPMCAS or HPMCP. However, the necessity to use such a large amount of plasticizer is a significant disadvantage.

The published Japanese Patent Application JP7070203A discloses a process wherein a hydroxycarboxylic acid type cellulose derivative is spread in water and pulverised by a pulveriser having a specific design to produce a cellulose derivative having a mean particle size below 7 microns, especially below 5 microns.

International Patent Application WO 2013/164122 discloses an aqueous composition for the manufacture of capsule shells comprising 5-50 wt. % of a wide range of functional polymers. In the majority of the examples the capsules are produced from an Aquacoat CPD 30 dispersion, which is a 30 wt. % aqueous dispersion comprising 23 wt. % non-salified cellulose acetate phthalate (CAP) and 7 wt. % Poloxamer, optionally blended with a minor amount of a HPMCAS slurry. Often uniform films can be obtained. A HPMCAS dispersion comprising 14% solids is also disclosed. Although 20% triethyl citrate is used as a film forming aid, when pins are heated to 50° C. and dipped into the dispersion, the HPMCAS polymer aggregates but the film rapidly collapses and flows down. A HPMCAS content of more than 14% in an aqueous dispersion would be desirable to increase the efficiency of preparing films and capsules. Unfortunately, an increased content of HPMCAS solids in the aqueous dispersion has the disadvantage of an increased viscosity at room temperature, i.e. at 20° C. However, a sufficiently low viscosity at about 20° C. is highly desirable. The dispersion should have a good flowability at 20° C. to facilitate its handling. Cooling the dispersion below 20° C. adds complexity and increases energy costs and is therefore not desirable.

HPMCAS particles become tacky and agglomerate in aqueous dispersions at elevated temperatures. This is desirable when the aqueous dispersion is not subjected to high shear, e.g. when the aqueous dispersion is heated for forming films under no or only gentle stirring. However, tackiness and agglomeration of HPMCAS particles is undesirable when the HPMCAS particles are subjected to high shear, e.g. when HPMCAS particles are to be mixed with other materials during preparation of HPMCAS dispersions at temperatures of more than 30° C.

Accordingly, it is an object of the present invention to provide aqueous compositions comprising dispersed esterified cellulose ethers which have a sufficiently low viscosity at a temperature of 20° C. to enable good flowability of the aqueous compositions. It is a preferred object of the present invention that such sufficiently low viscosity at 20° C. is achieved even when the aqueous compositions comprise at least 15 wt. % esterified cellulose ether, or even at least 20 wt. % esterified cellulose ether, or under optimized conditions even at least 25 wt. % esterified cellulose ether. It is another preferred object of the present invention to minimize tackiness or agglomeration of esterified cellulose ether particles when the particles are subjected to high shear, e.g., during the preparation of aqueous compositions comprising the esterified cellulose ether particles, even when the preparation of the aqueous compositions under high shear takes place at a temperature above 30° C.

SUMMARY

One aspect of the present invention is an aqueous composition which comprises a) at least one dispersed esterified cellulose ether comprising (i) groups of the formula —C(O)—R—COOA or (ii) a combination of aliphatic monovalent acyl groups and groups of the formula —C(O)—R—COOA, wherein R is a divalent aliphatic or aromatic hydrocarbon group and A is hydrogen or a cation, and b) from 0.05 to 20 percent of at least one salt of a fatty acid, based on the weight of the dispersed esterified cellulose ether, wherein the median particle size, d50, of the dispersed esterified cellulose ether particles is up to 7 micrometers, such median particle size (d50) being the size at which 50 mass percent of the particles have a smaller equivalent diameter and 50 mass percent have a larger equivalent diameter.

Another aspect of the present invention is a process for producing the above-mentioned aqueous composition, wherein the process comprises the steps of grinding, in the presence of an aqueous diluent, at least one esterified cellulose ether comprising (i) groups of the formula —C(O)—R—COOA or (ii) a combination of aliphatic monovalent acyl groups and groups of the formula —C(O)—R—COOA, wherein R is a divalent aliphatic or aromatic hydrocarbon group and A is hydrogen or a cation, and blending from 0.05 to 20 percent of at least one salt of a fatty acid and optionally one or more adjuvants with the esterified cellulose ether before, during or after the grinding of the esterified cellulose ether, the percentage of the fatty acid salt being based on the weight of the esterified cellulose ether.

Yet another aspect of the present invention is a process for producing the above-mentioned aqueous composition, wherein the process comprises the steps of melting a) an esterified cellulose ether comprising
(i) groups of the formula —C(O)—R—COOA or (ii) a combination of aliphatic monovalent acyl groups and groups of the formula —C(O)—R—COOA, wherein R is a divalent aliphatic or aromatic hydrocarbon group and A is hydrogen or a cation, and emulsifying the molten esterified cellulose ether in b) an aqueous diluent, adding c) from 0.05 to 20 percent of a salt of a fatty acid, based on the weight of the dispersed esterified cellulose ether, and optionally d) one or more adjuvants before, during or after the step of emulsifying the molten esterified cellulose ether in the aqueous diluent, and cooling the emulsion to form an aqueous dispersion.

Yet another aspect of the present invention is a dosage form which is coated with a coating prepared from the above-mentioned aqueous composition.

Yet another aspect of the present invention is a capsule shell which is made from the above-mentioned aqueous composition.

Yet another aspect of the present invention is a process for producing a capsule shell which comprises the steps of providing the above-mentioned aqueous composition, preheating molding pins to a temperature higher than the aqueous composition, dipping the pre-heating molding pins into the aqueous composition, forming a film on said molding pins by withdrawing said pins from said aqueous composition, and drying the film on the molding pins.

DESCRIPTION OF EMBODIMENTS

Figure 1:
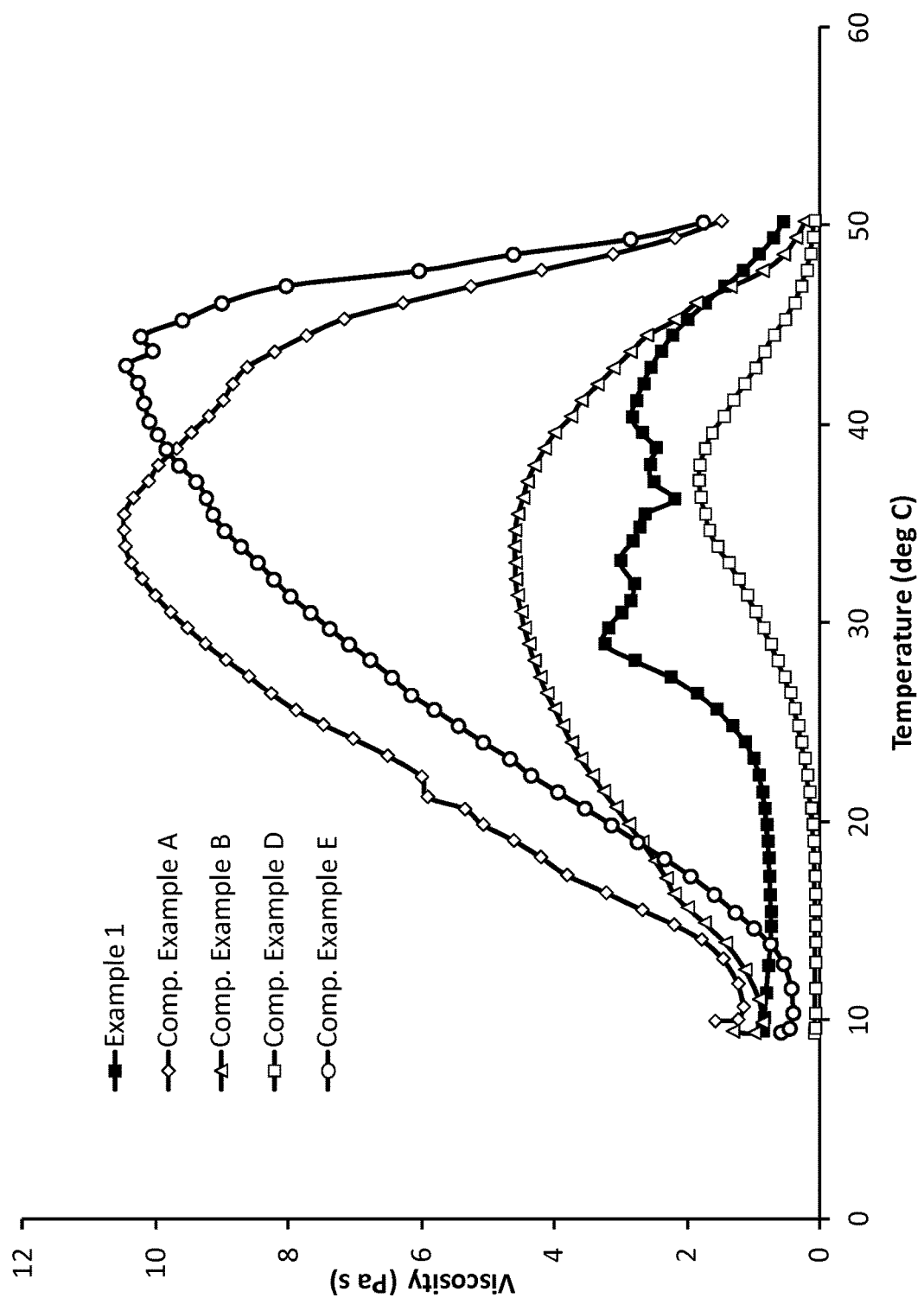
FIG. 1 illustrates the viscosity of three aqueous compositions of the present invention and of a comparative aqueous composition depending on its temperature.

Surprisingly, it has been found that the new aqueous compositions as described below have a sufficiently low viscosity at 20° C. to enable good flowability of the aqueous compositions, even when the aqueous compositions comprise at least 15 wt. % esterified cellulose ether, or even at least 20 wt. % esterified cellulose ether, or under optimized conditions even at least 25 wt. % esterified cellulose ether.

Surprisingly, it has also been found that new aqueous compositions comprising dispersed esterified cellulose ether(s) of fine particle sizes as described below can be prepared even at a temperature above 30° C. or even above 35° C., and generally up to about 45° C. The dispersed esterified cellulose ether(s) do not exhibit undue tackiness or agglomeration during preparation of the new aqueous compositions. The reduced tackiness and agglomeration at temperatures of more than 30° C. is important in many processing steps that require high shear, e.g., in those embodiments of the production process where the new aqueous compositions are produced by grinding esterified cellulose ether particles in the presence of water. Heat is generated during the grinding process. Excessively tacky esterified cellulose ether can lead to plugging of the milling apparatus and operation failures.

The esterified cellulose ether comprised in the composition of the present invention has a cellulose backbone having β-1,4 glycosidically bound D-glucopyranose repeating units, designated as anhydroglucose units in the context of this invention. The esterified cellulose ether preferably is an esterified alkyl cellulose, hydroxyalkyl cellulose or hydroxyalkyl alkylcellulose. This means that in the esterified cellulose ether comprised in the composition of the present invention, at least a part of the hydroxyl groups of the anhydroglucose units are substituted by alkoxyl groups or hydroxyalkoxyl groups or a combination of alkoxyl and hydroxyalkoxyl groups. The hydroxyalkoxyl groups are typically hydroxymethoxyl, hydroxyethoxyl and/or hydroxypropoxyl groups. Hydroxyethoxyl and/or hydroxypropoxyl groups are preferred. Typically one or two kinds of hydroxyalkoxyl groups are present in the esterified cellulose ether. Preferably a single kind of hydroxyalkoxyl group, more preferably hydroxypropoxyl, is present. The alkoxyl groups are typically methoxyl, ethoxyl and/or propoxyl groups. Methoxyl groups are preferred. Illustrative of the above-defined esterified cellulose ethers are esterified alkylcelluloses, such as esterified methylcelluloses, ethylcelluloses, and propylcelluloses; esterified hydroxyalkylcelluloses, such as esterified hydroxyethylcelluloses, hydroxypropylcelluloses, and hydroxybutylcelluloses; and esterified hydroxyalkyl alkylcelluloses, such as esterified hydroxyethyl methylcelluloses, hydroxymethyl ethylcelluloses, ethyl hydroxyethylcelluloses, hydroxypropyl methylcelluloses, hydroxypropyl ethylcelluloses, hydroxybutyl methylcelluloses, and hydroxybutyl ethylcelluloses; and those having two or more hydroxyalkyl groups, such as esterified hydroxyethylhydroxypropyl methylcelluloses. Most preferably, the esterified cellulose ether is an esterified hydroxyalkyl methylcellulose, such as an esterified hydroxypropyl methylcellulose.

The degree of the substitution of hydroxyl groups of the anhydroglucose units by hydroxyalkoxyl groups is expressed by the molar substitution of hydroxyalkoxyl groups, the MS(hydroxyalkoxyl). The MS(hydroxyalkoxyl) is the average number of moles of hydroxyalkoxyl groups per anhydroglucose unit in the esterified cellulose ether. It is to be understood that during the hydroxyalkylation reaction the hydroxyl group of a hydroxyalkoxyl group bound to the cellulose backbone can be further etherified by an alkylating agent, e.g. a methylating agent, and/or a hydroxyalkylating agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone.

The term "hydroxyalkoxyl groups" thus has to be interpreted in the context of the MS(hydroxyalkoxyl) as referring to the hydroxyalkoxyl groups as the constituting units of hydroxyalkoxyl substituents, which either comprise a single hydroxyalkoxyl group or a side chain as outlined above, wherein two or more hydroxyalkoxyl units are covalently bound to each other by ether bonding. Within this definition it is not important whether the terminal hydroxyl group of a hydroxyalkoxyl substituent is further alkylated or not; both alkylated and non-alkylated hydroxyalkoxyl substituents are included for the determination of MS(hydroxyalkoxyl). The esterified cellulose ether generally has a molar substitution of hydroxyalkoxyl groups of at least 0.05, preferably at least 0.08, more preferably at least 0.12, and most preferably at least 0.15. The degree of molar substitution is generally not more than 1.00, preferably not more than 0.90, more preferably not more than 0.70, and most preferably not more than 0.50.

The average number of hydroxyl groups substituted by alkoxyl groups, such as methoxyl groups, per anhydroglucose unit, is designated as the degree of substitution of alkoxyl groups, DS(alkoxyl). In the above-given definition of DS, the term "hydroxyl groups substituted by alkoxyl groups" is to be construed within the present invention to include not only alkylated hydroxyl groups directly bound to the carbon atoms of the cellulose backbone, but also alkylated hydroxyl groups of hydroxyalkoxyl substituents bound to the cellulose backbone. The esterified cellulose ethers preferably have a DS(alkoxyl) of at least 1.0, more preferably at least 1.1, even more preferably at least 1.2, most preferably at least 1.4, and particularly at least 1.6. The DS(alkoxyl) is preferably not more than 2.5, more preferably not more than 2.4, even more preferably not more than 2.2, and most not more than 2.05.

Most preferably the esterified cellulose ether is an esterified hydroxypropyl methylcellulose having a DS(methoxyl) within the ranges indicated above for DS(alkoxyl) and an MS(hydroxypropoxyl) within the ranges indicated above for MS(hydroxyalkoxyl).

The esterified cellulose ether utilized in the present invention has (i) groups of the formula —C(O)—R—COOA or (ii) a combination of aliphatic monovalent acyl groups and groups of the formula —C(O)—R—COOA, wherein R is a divalent aliphatic or aromatic hydrocarbon group and A is hydrogen or a cation. The cation preferably is an ammonium cation, such as $NH_4^+$ or an alkali metal ion, such as the sodium or potassium ion, more preferably the sodium ion. Most preferably, A is hydrogen.

The aliphatic monovalent acyl groups are preferably selected from the group consisting of acetyl, propionyl, and butyryl, such as n-butyryl or i-butyryl.

Preferred groups of the formula —C(O)—R—COOA are
—C(O)—CH$_2$—CH$_2$—COOA, such as —C(O)—CH$_2$—CH$_2$—COOH or —C(O)—CH$_2$—CH$_2$—COO$^-$Na$^+$,
—C(O)—CH═CH—COOA, such as —C(O)—CH═CH—COOH or —C(O)—CH═CH—COO$^-$Na$^+$, or
—C(O)—C$_6$H$_4$—COOA, such as —C(O)—C$_6$H$_4$—COOH or —C(O)—C$_6$H$_4$—COO$^-$Na$^+$.

In the groups of formula —C(O)—C$_6$H$_4$—COOA the carbonyl group and the carboxylic group are preferably arranged in ortho-positions.

Preferred esterified cellulose ethers are
i) HPMCXY, wherein HPMC is hydroxypropyl methyl cellulose, X is A (acetate), or X is B (butyrate) or X is Pr (propionate) and Y is S (succinate), or Y is P (phthalate) or Y is M (maleate), such as hydroxypropyl methyl cellulose acetate phthalate (HPMCAP), hydroxypropyl methyl cellulose acetate maleate (HPMCAM), or hydroxypropyl methylcellulose acetate succinate (HPMCAS), or ii) hydroxypropyl methyl cellulose phthalate (HPMCP), hydroxypropyl cellulose acetate succinate (HPCAS), hydroxybutyl methyl cellulose propionate succinate (HBMCPrS), hydroxyethyl hydroxypropyl cellulose propionate succinate (HEHPCPrS); and methyl cellulose acetate succinate (MCAS).

Hydroxypropyl methylcellulose acetate succinate (HPMCAS) is the most preferred esterified cellulose ether.

The esterified cellulose ethers generally have a degree of substitution of aliphatic monovalent acyl groups, such as acetyl, propionyl, or butyryl groups, of not more than 1.75, preferably not more than 1.50, more preferably not more than 1.25, and most preferably not more than 1.00, or even not more than 0.65. The degree of substitution of aliphatic monovalent acyl groups can be zero, but preferably it is at least 0.05, more preferably at least 0.10, and most preferably at least 0.20.

The esterified cellulose ethers generally have a degree of substitution of groups of formula —C(O)—R—COOA, such as succinoyl, of at least 0.05, preferably at least 0.10. The degree of substitution of groups of formula —C(O)—R—COOA generally is up to 1.6, preferably up to 1.30, more preferably up to 1.00, and most preferably up to 0.70 or even up to 0.60.

The sum of i) the degree of substitution of aliphatic monovalent acyl groups and ii) the degree of substitution of groups of formula —C(O)—R—COOA is generally at least 0.05, preferably at least 0.10, more preferably at least 0.20, most preferably at least 0.30, and particularly at least 0.40. The mentioned sum is generally no more than 2.0, preferably no more than 1.4, more preferably no more than 1.15, most preferably no more than 1.10 and particularly no more than 1.00.

The content of the acetate and succinate ester groups is determined according to "Hypromellose Acetate Succinate", United States Pharmacopeia and National Formulary, NF 29, pp. 1548-1550. Reported values are corrected for volatiles (determined as described in section "loss on drying" in the above HPMCAS monograph). The method may be used in analogue manner to determine the content of propionyl, butyryl, phthalyl and other ester groups.

The content of ether groups in the esterified cellulose ether is determined in the same manner as described for "Hypromellose", United States Pharmacopeia and National Formulary, USP 35, pp 3467-3469.

The contents of ether and ester groups obtained by the above analyses are converted to DS and MS values of individual substituents according to the formulas below. The formulas may be used in analogue manner to determine the DS and MS of substituents of other cellulose ether esters.

$$\% \text{ cellulose backbone} = 100 - \left(\% \text{ MeO} * \frac{M(OCH_3) - M(OH)}{M(OCH_3)}\right) -$$
$$\left(\% \text{ HPO} * \frac{M(OCH_2CH(OH)CH_3) - M(OH)}{M(OCH_2CH(OH)CH_3)}\right) -$$
$$\left(\% \text{ Acetyl} * \frac{M(COCH_3)M(H)}{M(COCH_3)}\right) -$$
$$\left(\% \text{ Succinoyl} * \frac{M(COC_2H_4COOH) - M(H)}{M(COC_2H_4COOH)}\right)$$

$$DS(\text{Me}) = \frac{\dfrac{\% \text{ MeO}}{M(\text{OCH}_3)}}{\dfrac{\% \text{ cellulose backbone}}{M(\text{AGU})}} \quad MS(\text{HP}) = \frac{\dfrac{\% \text{ HPO}}{M(\text{HPO})}}{\dfrac{\% \text{ cellulose backbone}}{M(\text{AGU})}}$$

$$DS(\text{Acetyl}) = \frac{\dfrac{\% \text{ Acetyl}}{M(\text{Acetyl})}}{\dfrac{\% \text{ cellulose backbone}}{M(\text{AGU})}}$$

$$DS(\text{Succinoyl}) = \frac{\dfrac{\% \text{ Succinoyl}}{M(\text{Succinoyl})}}{\dfrac{\% \text{ cellulose backbone}}{M(\text{AGU})}}$$

$$M(\text{MeO}) = M(\text{OCH}_3) = 31.03 \text{ Da}$$

$$M(\text{HPO}) = M(\text{OCH}_2\text{CH(OH)CH}_3) = 75.09 \text{ Da}$$

$$M(\text{Acetyl}) = M(\text{COCH}_3) = 43.04 \text{ Da}$$

$$M(\text{Succinoyl}) = M(\text{COC}_2\text{H}_4\text{COOH}) = 101.08 \text{ Da}$$

$$M(\text{AGU}) = 162.14 \text{ Da} \quad M(\text{OH}) = 17.008 \text{ Da} \quad M(\text{H}) = 1.008 \text{ Da}$$

By convention, the weight percent is an average weight percentage based on the total weight of the cellulose repeat unit, including all substituents. The content of the methoxyl group is reported based on the mass of the methoxyl group (i.e., —$OCH_3$). The content of the hydroxyalkoxyl group is reported based on the mass of the hydroxyalkoxyl group (i.e., —O-alkylene-OH); such as hydroxypropoxyl (i.e., —O—$CH_2CH(CH_3)$—OH). The content of the aliphatic monovalent acyl groups is reported based on the mass of —C(O)—$R_1$ wherein $R_1$ is a monovalent aliphatic group, such as acetyl (—C(O)—$CH_3$). The content of the group of formula —C(O)—R—COOH is reported based on the mass of this group, such as the mass of succinoyl groups (i.e., —C(O)—$CH_2$—$CH_2$—COOH).

The esterified cellulose ether comprised in the composition of the present invention generally has a viscosity of at least 1.2 mPa·s, preferably least 1.8 mPa·s, and more preferably least 2.4 mPa·s, and generally no more than 200 mPa·s, preferably no more than 100 mPa·s, more preferably no more than 50 mPa·s, and most preferably no more than 30 mPa·s, measured as a 2.0 weight percent solution of the esterified cellulose ether in 0.43 wt % aqueous NaOH at 20° C. according to "Hypromellose Acetate Succinate, United States Pharmacopia and National Formulary, NF 29, pp. 1548-1550".

The aqueous composition of the present invention generally comprises at least 5 percent, preferably at least 10 percent, more preferably at least 15 percent, most preferably at least 20 percent, and under some conditions even at least 25 percent of the esterified cellulose ether(s) in dispersed state in the aqueous composition. The aqueous composition of the present invention generally comprises up to 40 percent or up to 35 percent of the esterified cellulose ether(s) in dispersed state in the aqueous composition.

The rheological profile of the aqueous composition is important to its usefulness for coating substrates, such as dosage forms like tablets, and for producing capsule shells. The aqueous composition should have a reasonably low viscosity at 20° C. to facilitate processing operations during capsule manufacturing or coating processes.

Upon heating of the aqueous composition without shear or with only low shear, e.g., at a shear of not more than 1000 $sec^{-1}$, its viscosity should increase to adhere to the surface of the substrate to be coated, such as tablets, or to metal pins in the case of capsule production. Finally the esterified cellulose ether particles should coagulate and form a film. It is known to include a surfactant in an aqueous dispersion comprising an esterified cellulose ether to stabilize the dispersion, i.e., to keep the esterified cellulose ether particles dispersed in the aqueous phase. A huge variety of anionic, cationic and non-ionic surfactants exists. Well-known anionic surfactants are sodium alkyl sulfates, such as sodium dodecyl sulfate. Well-known non-ionic surfactants are ethylene oxide-propylene oxide block copolymers, such as Pluronic™ surfactants, or polyoxyethylene sorbitan monooleates, such as Polysorbate 80, also known under the trademark Tween 80. Unfortunately, aqueous compositions having a high concentration of dispersed esterified cellulose ether, such as 20 wt.-% or more, and an above-mentioned surfactant like a Pluronic™ surfactant or a polyoxyethylene sorbitan monooleate have a very high viscosity at 20° C., typically higher than 2500 mPa·s, and often even higher than 3000 mPa·s.

Surprisingly, it has been found that an aqueous composition of the present invention, even when comprising a high concentration of dispersed esterified cellulose ether, has a reasonably low viscosity at 20° C. when the aqueous composition comprises a salt of a fatty acid, preferably an ammonium, alkali metal or alkaline earth metal salt of a saturated or unsaturated fatty acid. The apparent viscosity is considerably lower than when the composition comprises a comparable amount of another surfactant. The viscosity of the aqueous composition of the present invention is generally 20 mPa·s or more, typically 25 mPa·s or more, measured at 20° C. The apparent viscosity of the aqueous composition of the present invention is generally no more than 2000 mPa·s, typically no more than 1500 mPa·s, and under optimized conditions no more than 1000 mPa·s or even no more than 500 mPa·s, measured at 20° C.

Surprisingly, it has also been found that the new aqueous compositions as described below do not exhibit undue tackiness or agglomeration of the esterified cellulose ether particles during preparation of the new aqueous compositions under high shear, for example by grinding esterified cellulose ether particles in the presence of water and a salt of a fatty acid, at a temperature above 30° C. or even above 40° C., and generally up to 45° C.

A great advantage of the dispersion of the present invention is its response to deformation over a range of shear rates and temperatures. Below about 1000 $sec^{-1}$, i.e., at low shear, the viscosity of the dispersion increases and it adheres to the surface of the substrate to be coated when it is heated. Finally the continuous phase is evaporated during the coating and drying process to form a film. At high shear, the esterified cellulose ether particles do not exhibit substantial agglomeration or tackiness when heated in a sealed system, e.g., up to 45° C., where the continuous phase does not evaporate.

Accordingly, the aqueous composition further comprises from 0.05 to 20 percent of at least one salt of a fatty acid, based on the weight of the dispersed esterified cellulose ether. The total amount of the salt(s) of a fatty acid preferably is at least 0.1 percent, more preferably at least 0.3 percent, even more preferably at least 0.5 percent, most preferably at least 0.8 percent, and particularly at least 1.0 percent, based on the total weight of the esterified cellulose ether(s). The total amount of the salt(s) of a fatty acid preferably is up to 15 percent, more preferably up to 12 percent, even more preferably up to 10 percent or 8 percent, and most preferably up to 6.0 percent, or even only up to 5.0 percent, based on the total weight of the esterified cellulose ether(s).

Preferred fatty acid salts are ammonium, alkali metal or alkaline earth metal salts. A preferred ammonium ion is $NH_4^+$. Preferred alkali metal ions are the sodium or potassium ions. A preferred alkaline earth metal ion is the calcium ion. The fatty acids can be saturated or unsaturated. Exemplary of saturated fatty acids are caprylic acid, capric acid, lauric acid, myristic acid, palmitic acid, stearic acid, arachidic acid, behenic acid, lignoceric acid and cerotic acid. The unsaturated fatty acids can be mono-, di- or triunsaturated fatty acids, mono-unsaturated and di-unsaturated fatty acids being preferred. Exemplary of mono-unsaturated fatty acids are myristoleic acid, palmitoleic acid, sapienic acid, oleic acid, elaidic acid and vaccenic acid. Exemplary of di-unsaturated fatty acids are linoleic acid and linoelaidic acid. Ammonium, alkali metal and alkaline earth metal salts of stearic acid or oleic acid are most preferred, particularly those salts mentioned above.

The aqueous composition of the present invention is in the form of an aqueous dispersion, typically in the form of a stable dispersion. The median particle size, d50, of the dispersed esterified cellulose ether particles is up to 7 micrometers, typically up to 5 micrometers, even more typically up to 3 micrometers, and most typically even only up to 2 micrometers. The median particle size, d50, of the dispersed esterified cellulose ether particles is typically 0.3 micrometers or more, more typically 0.5 micrometers or more, and most typically 0.7 micrometers or more. The particle size is measured by laser diffraction particle size analysis, e.g., using a Beckman Coulter laser diffraction particle size analyzer which is commercially available from Beckman Coulter, California. The median particle size d50 is the diameter where 50 mass percent of the particles have a smaller equivalent diameter and 50 mass percent have a larger equivalent diameter. Typically d90 is 0.7 micrometers or more, more typically 1.0 micrometers or more, and most typically 1.5 micrometers or more; and typically up to 12 micrometers, more typically up to 10 micrometers, even more typically up to 9 micrometers, most typically up to 7 micrometers and in many cases even only up to 5 micrometers, d90 being the diameter where 90 mass percent of the particles have a smaller equivalent diameter and the other 10 mass percent have a larger equivalent diameter. The equivalent particle diameter d is the diameter of a sphere having the same volume as the volume of a given particle. The mean particle diameter is typically 0.5 micrometers or more, more typically 0.7 micrometers or more, and most typically 0.8 micrometers or more; and typically up to 8 micrometers, more typically up to 6 micrometers, even more typically up to 4 micrometers, and most typically even only up to 3 micrometers.

The aqueous composition of the present invention comprises an aqueous diluent. The aqueous diluent is water, optionally mixed with a minor amount of an organic solvent. The aqueous diluent preferably consists of 50-100 weight percent, more preferably 65-100 weight percent, and most preferably 75-100 weight percent of water and preferably 0-50 weight percent, more preferably 0-35 weight percent, and most preferably 0-25 weight percent of an organic solvent, based on the total weight of water and the organic solvent. Useful organic solvents are polar organic solvents having one or more heteroatoms, such as oxygen, nitrogen or halogen like chlorine. More preferred organic solvents are alcohols, for example multifunctional alcohols, such as glycerol, or preferably monofunctional alcohols, such as methanol, ethanol, isopropanol or n-propanol; ethers, such as tetrahydrofuran, ketones, such as acetone; methyl ethyl ketone, or methyl isobutyl ketone; acetates, such as ethyl acetate; halogenated hydrocarbons, such as methylene chloride; or nitriles, such as acetonitrile. Preferably the aqueous composition of the present invention comprises water alone as aqueous diluent. The amount of the aqueous diluent is typically at least 50 percent, more typically at least 60 percent, and most typically at least 65 percent, based on the total weight of the aqueous composition. The amount of the aqueous diluent is typically no more than 85 percent, more typically no more than 80 percent, and most typically no more than 75 percent, based on the total weight of the aqueous composition.

In one embodiment the sum of a) the esterified cellulose ether(s) described above and b) the salt(s) of a fatty acid amounts to at least 50 percent, typically at least 60 percent, and more typically at least 80 percent; and up to 100 percent, typically up to 99 percent, more typically up to 95 percent, and most typically up to 90 percent of the total weight of the ingredients of the aqueous composition excluding the aqueous diluent.

The aqueous composition of the present invention may further comprise optional ingredients, for example active ingredients, such as fertilizers, herbicides or pesticides, or biologically active ingredients, such as vitamins, herbals and mineral supplements and drugs; or adjuvants such as one or more plasticizers, film forming aids, coloring agents, pigments, opacifiers, flavor and taste improvers, antioxidants, and any combination thereof. Optional additives are preferably pharmaceutically acceptable. The amount of these optional ingredients is typically from 0 to 50 percent of the total weight of the ingredients of the aqueous composition excluding the aqueous diluent. Typically the amount is 1 percent or more, more typically 5 percent or more, and most typically 10 percent or more; and up to 40 percent, more typically up to 20 percent, and most typically up to 10 percent of the total weight of the ingredients of the aqueous composition excluding the aqueous diluent.

In one embodiment, the aqueous composition of the present invention further comprises at least one film forming aid. The term "film forming aid" comprises one or more plasticizers conventionally used in the manufacture of coatings or capsule shells, notably hard capsule shells, to ensure the formation of self-supported cohesive films and avoid capsule brittleness, and/or one or more viscosity enhancers at elevated temperature, i.e. natural as well as synthetic substances conventionally used to optimize aqueous compositions for coating purposes or the dip molding manufacture of hard capsule shells.

Film forming aids that display plasticizing properties include: phthalic esters, such as dimethyl-, diethyl-, and diisopropyl-phthalate; citric esters, such as triethyl-, tributyl-, acetyltriethyl- and acetyltributyl-citrate; phosphoric esters, such as triethyl-, tricresyl, and triphenyl-phosphate; alkyl lactate; glycol esters; glycerol and glycerol esters, such as glycerol triacetate also known as triacetine; sucrose esters; oils and fatty acid esters; butyl stearate; dibutyl sebacate; dibutyl tartrate; diisobutyl adipate, tributyrin; propylene glycol; and mixtures thereof.

In one embodiment, film forming aids are cellulose ethers, such as carboxy methylcellulose, hydroxypropyl cellulose, ethyl cellulose, methylcellulose, hydroxypropylmethylcellulose (HPMC), e.g. HPMC types 2910, 2906 and/or 2208 as defined in USP30-NF25; gelatin, pullulan, non enteric starch derivatives, such as hydroxypropyl starch; polyvinyl acetate derivatives (PVAP); sorbitan monoesters; sorbitan polyoxyethylene esters; fatty acid esters; glycerol polyethylene, glycol ricinoleate; macrogolglycerides; triethyl citrate (TEC); acetyl trialkyl citrate; glycerol triacetate (triacetine); talc; and mixtures thereof.

In one embodiment, one or more film forming aids are present in the aqueous composition in an amount ranging from 0 to 20% by weight, such as 0 to about 15% by weight, or 0 to 10% by weight, based on the total weight of the aqueous composition of the present invention.

In one embodiment the aqueous composition of the present invention, which comprises at least one dispersed esterified cellulose ether and at least one salt of a fatty acid as described above, additionally comprises at least 5 percent, more preferably at least 10 percent, even more preferably at least 13 percent, and most preferably at least 15 percent of one or more plasticizers, based on the weight of the dispersed esterified cellulose ether. The amount of said one or more plasticizers is generally up to 30 percent, preferably up to 25 percent, even more preferably up to 22 percent, and most preferably up to 20 percent, based on the weight of the dispersed esterified cellulose ether.

In a preferred embodiment the aqueous composition comprises two or three plasticizers, more preferably three plasticizers, selected from i) citric ester(s), ii) ester(s) of dicarboxylic acid(s), and iii) acetoglyceride(s) or block copolymer(s) comprising blocks of poly(ethylene oxide) and poly(propylene oxide), provided that two or three plasticizers, preferably three plasticizers, are selected from different groups i)-iii). The total weight percentage of i) the citric esters, ii) the esters of dicarboxylic acids, and iii) the acetoglycerides or block copolymers comprising blocks of poly(ethylene oxide) and poly(propylene oxide) is preferably as described above. In a more preferred embodiment the plasticizer combination comprises at least 1 weight part, preferably at least 3 weight parts, more preferably at least 5 weight parts, and most preferably at least 6 weight parts of a citric ester and of an ester of a dicarboxylic acid, each independently, per weight part of an acetoglyceride or a block copolymer comprising blocks of poly(ethylene oxide) and poly(propylene oxide). The amount of a citric ester and of an ester of a dicarboxylic acid, each independently, is preferably up to 30 weight parts, more preferably up to 20 weight parts, even more preferably up to 15 weight parts, and most preferably up to 9 weight parts, per weight part of acetoglyceride or block copolymer comprising blocks of poly(ethylene oxide) and poly(propylene oxide).

Preferred citric esters of group i) are triethyl-, tributyl-, acetyltriethyl- and acetyltributyl-citrate. Triethyl citrate is the most preferred citric ester.

Preferred esters, more preferably diesters, of a dicarboxylic acid of group ii) are adipates, sebacates or maleates, such as bis(2-ethylhexyl)adipate, dimethyl adipate, monomethyl adipate, dibutyl sebacate (DBS), dibutyl maleate, or diisobutyl maleate. The most preferred diester of a dicarboxylic acid is dibutyl sebacate.

Useful plasticizers of group iii) are acetoglycerides or block copolymers comprising blocks of poly(ethylene oxide) and poly(propylene oxide). Preferred acetoglycerides are, for example, mono-acetylated monoglycerides, diacetylated monoglycerides, or mono-acetylated diglycerides. Diacetylated monoglycerides are preferred. Glycerides are esters formed from glycerol and a fatty acid. The fatty acid can be saturated or unsaturated. Exemplary of saturated fatty acids are caprylic acid, capric acid, lauric acid, myristic acid, palmitic acid, stearic acid, arachidic acid, behenic acid, lignoceric acid and cerotic acid. The unsaturated fatty acids can be mono-, di- or triunsaturated fatty acids, mono-unsaturated and di-unsaturated fatty acids being preferred. Exemplary of mono-unsaturated fatty acids are myristoleic acid, palmitoleic acid, sapienic acid, oleic acid, elaidic acid and vaccenic acid. Exemplary of di-unsaturated fatty acids are linoleic acid and linoelaidic acid. Preferred block copolymers comprising blocks of poly(ethylene oxide) and poly(propylene oxide) are ethylene oxide/propylene oxide block copolymers, or ethylene oxide/propylene oxide/ethylene oxide block copolymers, also known as poloxamers. Poloxamers are nonionic triblock copolymers composed of a central hydrophobic chain of polyoxypropylene (poly(propylene oxide)) flanked by two hydrophilic chains of polyoxyethylene (poly(ethylene oxide)). Preferred poloxamers have a number average molecular weight, measured by gel permeation chromatography (GPC), of more than 500, preferably of more than 900, even more preferably of more than 2000, and most preferably of more than 3500. The number average molecular weight is generally less than 20,000, preferably less than 15,000, more preferably less than 10,000, and most preferably less than 6000. The weight of polyethylene oxide in the block copolymer is generally at least 2 percent, preferably at least 5 percent, and more preferably at least 7 percent. The weight of polyethylene oxide in the block copolymer is generally up to 90 percent, preferably up to 50 percent, and more preferably up to 20 percent, based on the total weight of the block copolymer. Most preferably, the poloxamer is liquid at 20° C. and atmospheric pressure. The most preferred poloxamer is commercially available under the trademark Pluronic L121 from BASF Corporation. Other preferred block copolymers comprising blocks of poly(ethylene oxide) and poly(propylene oxide) are commercially available under the trademark Pluronic 17R2, and Pluronic L62 from BASF Corporation.

The aqueous composition of the present invention can be prepared by various methods. One method includes grinding the esterified cellulose ether in the presence of an aqueous diluent and optionally in the presence of one or more adjuvants. Another method includes melting or softening the esterified cellulose ether at an elevated temperature, optionally in the presence of one or more adjuvants, and emulsifying the molten or softened mass in the aqueous diluent. Preparing an aqueous composition by simply physically blending an esterified cellulose ether, a salt of a fatty acid and an aqueous diluent at room temperature is usually not suitable for preparing a stable dispersion.

In one embodiment the process for producing the aqueous composition of the present invention comprises the steps of grinding, in the presence of an above-described aqueous diluent, at least one esterified cellulose ether as described above, and blending from 0.05 to 20 percent (based on the weight of the esterified cellulose ether) of at least one salt of a fatty acid and optionally one or more adjuvants with the esterified cellulose ether before, during or after the grinding of the esterified cellulose ether. Any grinding device suitable for grinding esterified cellulose ethers in the presence of an aqueous diluent to a median particle size d50 as indicated further above can be used. Preferred grinding devices are wet grinding units such as media mills or bead mills. The grinding is typically conducted at a temperature of at least 2° C., more typically at least 15° C., and typically at a temperature of up to 40° C., more typically up to 35° C. Grinding is conducted for a sufficient time period to achieve an above-mentioned median particle size, d50, of the dispersed esterified cellulose ether particles.

In another embodiment the process for producing the aqueous composition of the present invention comprises the steps of melting a) at least one esterified cellulose ether as described above and emulsifying the molten esterified cellulose ether in b) an above-described aqueous diluent, adding c) from 0.05 to 20 percent of an above-described salt of a fatty acid, based on the weight of the dispersed esterified cellulose ether, and optionally d) one or more adjuvants before, during or after the step of emulsifying the molten esterified cellulose ether in the aqueous diluent, and cooling the emulsion to form an aqueous dispersion. This embodiment of the process is preferably conducted in an extruder. Alternatively, a pressurized batch kneader can be used for conducting this embodiment of the invention.

In a preferred embodiment the process for producing the aqueous composition of the present invention comprises the steps of melting the esterified cellulose ether and optionally one or more adjuvants in a melt zone of an extruder to form a melt, conveying the melt to an emulsification zone of the extruder in which the temperature and pressure are controlled; feeding aqueous diluent, one or more salts of a fatty acid, and optionally one or more adjuvants into the emulsification zone, wherein the melt is emulsified in the added components, conveying the produced emulsion to a dilution and cooling zone of the extruder; and feeding aqueous diluent, optionally one or more salts of a fatty acid, and optionally one or more adjuvants into the dilution and cooling zone to dilute the emulsion thereby forming an aqueous dispersion. The general process conditions and equipment which may be used to perform the process are disclosed in U.S. Pat. No. 5,539,021, the disclosure of which is incorporated herein by reference.

Alternatively, a pressurized batch kneader can be used for conducting the steps of melting an above-described esterified cellulose ether, emulsifying the molten esterified cellulose ether in an aqueous diluent, adding from 0.05 to 20 percent of a salt of a fatty acid and optionally one or more adjuvants before, during or after the step of emulsifying the molten esterified cellulose ether in the aqueous diluent, and cooling the emulsion to form an aqueous dispersion.

In the melt-extrusion processes described above the melting step is preferably conducted at a temperature of from 100 to 155° C., more preferably from 125 to 145° C., and at a pressure from 1 to 35 bar, more preferably from 15 to 25 bar. The emulsification step is preferably conducted at a temperature of from 100 to 155° C., more preferably from 115 to 135° C., and at a pressure from 4 to 35 bar, more preferably from 15 to 25 bar. The cooling step is preferably conducted at a temperature of from 45 to 100° C., more preferably from 70 to 90° C., and at a pressure from 1 to 35 bar, more preferably from 1 to 5 bar.

Suitable and preferred types and amounts of esterified cellulose ethers, salts of fatty acids, optional adjuvants and aqueous diluents in the processes for producing the aqueous composition of the present invention are described further above. The salt(s) of a fatty acid and optional adjuvants are preferably added before or during the grinding of the esterified cellulose ether or the step of emulsifying the molten esterified cellulose ether in the aqueous diluent. A salt of a fatty acid and optional adjuvants can also be added after the grinding of the esterified cellulose ether or after the step of emulsifying the molten esterified cellulose ether, but preferably at least 50 percent of the salt of a fatty acid that is used for preparing the aqueous composition of the present invention is added before or during the grinding or emulsification of the esterified cellulose ether.

In another aspect of the invention the aqueous composition of the present invention may be used for coating dosage forms, such as tablets, granules, pellets, caplets, lozenges, suppositories, pessaries or implantable dosage forms, to form a coated composition. If the aqueous composition of the present invention comprises an active ingredient, such as a drug, drug layering can be achieved, i.e., the dosage form and the coating may comprise different active ingredients for different end-uses and/or having different release kinetics. The coating can be carried out in a known manner, for example by known dipping or spraying processes.

In yet another aspect of the invention the aqueous composition of the present invention may be used for the manufacture of capsules shells in a process which comprises the step of contacting the aqueous composition with dipping pins. According to one embodiment the process for producing capsule shells comprises the steps of providing the aqueous composition of the present invention as described above, pre-heating molding pins to a temperature higher than the aqueous composition, dipping the pre-heated molding pins into the aqueous composition, forming a film on said molding pins by withdrawing said pins from said aqueous composition, and drying the film on the molding pins. The general process conditions and equipment which may be used to prepare capsules shells are described in International Patent Application Nos. WO 2013/164122 and WO 2013/164121, the disclosures of which are incorporated herein by reference.

The aqueous composition of the present invention is particularly useful for coating dosage forms including tablets, capsules and others, or for the formation of capsules shells, all preferably for enteric use, i.e., coatings or capsules shells that are dissolved in the intestinal canals to release the active ingredient like a drug contained in the dosage form or in the capsules.

Some embodiments of the invention will now be described in detail in the following Examples.

EXAMPLES

Unless otherwise mentioned, all parts and percentages are by weight. In the Examples the following test procedures are used.

Viscosity of Hydroxypropyl Methyl Cellulose Acetate Succinate (HPMCAS)

A 2.0% by weight solution of the HPMCAS in 0.43 wt % aqueous NaOH was prepared as described in "Hypromellose Acetate Succinate, United States Pharmacopia and National Formulary, NF 29, pp. 1548-1550, followed by an Ubbelohde viscosity measurement at 20° C. according to DIN 51562-1:1999-01 (January 1999).

Content of Ether and Ester Groups of HPMCAS

The content of ether groups in HPMCAS was determined in the same manner as described for "Hypromellose", United States Pharmacopeia and National Formulary, USP 35, pp 3467-3469.

The ester substitution with acetyl groups ($-CO-CH_3$) and the ester substitution with succinoyl groups ($-CO-CH_2-CH_2-COOH$) were determined according to Hypromellose Acetate Succinate, United States Pharmacopia and National Formulary, NF 29, pp. 1548-1550". Reported values for ester substitution were corrected for volatiles (determined as described in section "loss on drying" in the above HPMCAS monograph).

Apparent Viscosity of the Aqueous Composition

The apparent viscosity of the aqueous dispersion comprising HPMCAS was measured at various temperatures according to a temperature sweep experiment performed with a Anton Paar MCR 301 rheometer with a CC-27 cup geometry and a 4-blade vane geometry ST26-4V-20 over a temperature range of 10 to 50° C. with a heating rate of 3°

C./min and a constant speed of the vane geometry of 40 rpm and a measurement point duration of 0.2721 min. Prior to this temperature sweep testing the material was treated with a SpeedMixer™ DAC 150.1 FV (FlackTek Inc.) at 2300 rpm for 1 min to remove foam and air bubbles. A sample volume of 20 ml was used for these measurements. The samples had been stored at room temperature prior to the viscosity measurement.

Determination of Phase Transition Temperature of the Aqueous Composition

The obtained data of the apparent viscosity, which was obtained from the temperature sweep measurements above, was used for this analysis. The phase transition temperature of the aqueous composition is the temperature at which the HPMCAS particles start to gel and the viscosity of the aqueous composition starts to significantly increase.

The average viscosity of the aqueous composition at temperatures from 10 to 15° C. was calculated from the measured apparent viscosity data to determine the baseline viscosity of the aqueous composition. The standard deviation of the baseline viscosity was calculated. When the standard deviation was more than 25%, this was an indication that there was no constant viscosity at a temperature range from 10 to 15° C. and that the phase transition temperature was below 15° C. The phase transition temperature of the aqueous composition was determined to be the temperature at which the viscosity of the aqueous composition reached 150% of its baseline viscosity.

HPMCAS Particle Size Measurement in the Aqueous Dispersion

To measure particle sizes 1-2 g of the aqueous HPMCAS dispersion that had been produced as described below was diluted in 20 ml of purified water. The particle size in the diluted dispersion was measured by laser diffraction particle size analysis using a Beckman Coulter LS 13 320 laser diffraction particle size analyzer which is commercially available from Beckman Coulter, California. The Universal Liquid Module (ULM) with a Fraunhofer optical model, a Polarization Intensity Differential Scattering (PIDS) system and a sonication control unit were used. In the sonication control unit the HPMCAS dispersion was subjected to ultrasonic treatment for a time period of up to 120 seconds during the HPMCAS addition (about 30 seconds) and particle size measurement (about 90 seconds).

Stability Assessment

To assess the stability of the aqueous HPMCAS dispersion, the HPMCAS particle size measurement described above was repeated after about 2 weeks. The degree of changes in particle size was a clear indication of the stability of the aqueous HPMCAS dispersion. The dispersion was also visually inspected.

Determination of Solids Content

The solids content was determined using a moisture balance (Mettler Toledo Advanced Moisture Analyzer, Model HB43-S). Instrument settings were as follows: 3 g dispersion using the Rapid drying program with a temperature set point of 120° C. (40% overshoot for first 3 minutes) with switch-off criteria 5 (less than 1 mg weight change over 140 seconds). Upon drying to remove water, the residual solids content (including all additives) was weighed.

HPMCAS Used for Preparing the Aqueous Dispersion in Examples 1, 2, 5, 9, 10 and Comparative Examples A-E HPMCAS was used that had 23.7% methoxyl groups ($DS_{methoxyl}$=1.93), 7.1% hydroxypropoxyl groups ($MS_{hydroxypropoxyl}$=0.24), 9.6% acetyl groups ($DS_{acetyl}$=0.56), 10.5% succinoyl groups ($DS_{succinoyl}$=0.26), and a viscosity of 2.96 mPa·s, measured as a 2.0% by weight solution of the HPMCAS in 0.43 wt. % aqueous NaOH.

HPMCAS Used for Preparing the Aqueous Dispersion in Examples 3, 4, 6, 7, 8, 11, 12 and Comparative Example F HPMCAS was used that had 23.3% methoxyl groups ($DS_{methoxyl}$=1.92), 7.2% hydroxypropoxyl groups ($MS_{hydroxypropoxyl}$=0.24), 9.8% acetyl groups ($DS_{acetyl}$=0.58), 10.9% succinoyl groups ($DS_{succinoyl}$=0.28), and a viscosity of 2.68 mPa·s, measured as a 2.0% by weight solution of the HPMCAS in 0.43 wt. % aqueous NaOH.

HPMCAS Used for Preparing the Aqueous Dispersion in Example 13 and Comparative Example G HPMCAS was used that had 23.2% methoxyl groups ($DS_{methoxyl}$=1.90), 7.3% hydroxypropoxyl groups ($MS_{hydroxypropoxyl}$=0.25), 9.3% acetyl groups ($DS_{acetyl}$=0.55), 11.2% succinoyl groups ($DS_{succinoyl}$=0.28), and a viscosity of 2.91 mPas, measured as a 2.0% by weight solution of the HPMCAS in 0.43 wt % aqueous NaOH.

Example 1-6 and Comparative Examples A-E

To produce an aqueous HPMCAS dispersion, water was loaded first and recirculated through a Netzsch LAB STAR media mill (1.4 mm Ytterum Stabilized Zirconia media, 0.7 mm screen size). During the milling process HPMCAS solids and a surfactant as listed in Table 1 below were loaded gradually to water recirculating through the mill at a mill speed of 3600 rev/min. The HPMCAS and the surfactant were added at a predetermined weight ratio to provide a percentage of surfactant, based on HPMCAS, as listed in Table 1 below. Addition of HPMCAS and surfactant was continued until a total solids loading of 20-30% was achieved, based on the total weight of the composition. The percentages of HPMCAS and surfactant, each based on the total weight of the composition, were calculated from the measured solids content and the given weight ratio between HPMCAS and the surfactant. The results are listed in Table 1 below. Following the addition of all solids, milling continued until the final particle size was obtained.

Examples 1-6 and Comparative Examples A, B, D and E were completed using a similar procedure. In Comparative Example C no dispersion was obtained as the viscosity of the dispersion caused a pressure in the mill that exceeded the allowable pressure system.

In Comparative Example A no additive, i.e. no surfactant, was used. In Comparative Example B the well-known non-ionic surfactant polyoxyethylene (20) sorbitan monooleate, commercially available under the Trademark Tween 80 was used. In Comparative Examples C and D sodium dodecyl sulfate (SDS) was used, which is a well-known anionic surfactant. In Comparative Example E a block copolymer of ethylene oxide and propylene oxide, which is commercially available from BASF under the Trademark Pluronic L44 NF INH, was used as non-ionic surfactant. The results in Table 1 below illustrate that the viscosity of the dispersions of Comparative Examples A, B, and E was unduly high. Also, the dispersion of Comparative Example B had HPMCAS particles that were very large. In Example C no dispersion was obtained as the viscosity of the dispersion caused a pressure in the mill that exceeded the allowable system pressure. Example D produced a dispersion with acceptable viscosity and particle size but with some tendency to agglomerate upon storage for about 2 weeks. The dispersions of Comparative Examples A-E were not suitable for reasonably convenient handling and processing.

The results in Table 1 below also illustrate that the HPMCAS dispersions of Example 1-6, which contained a salt of a fatty acid, had HPMCAS of fine particle size, and had a sufficiently low viscosity at 20° C. to be of good flowability at room temperature. The dispersions of Examples 1, 4, 5 and 6 were visually inspected and their mean particle size was measured after about 2 weeks. They were stable, i.e., did not show undue sedimentation or formation of lumps. Examples 1, 4 and 6 comprising an alkali metal salt of a fatty acid as surfactant were very stable and did not tend to agglomerate. Example 5 comprising less than 0.5 wt. % of potassium stearate as a surfactant showed some agglomeration after about 2 weeks.

Examples 7-11 and Comparative Examples F and G

Example 1 was repeated, except that a Drais DCP-12 Advantis media mill (1.0 mm Ytterum Stabilized Zirconia media, 0.5 mm screen size) was used. The mill speed was initially set at 1600 rpm and then reduced as necessary down to about 1300 rpm to control the mill outlet temperature. The amount of sodium stearate and the final solids content were altered as shown in Table 1 below. Comparative Examples F and G were produced without surfactant.

The results in Table 1 below again illustrate that HPMCAS dispersions of Examples 7-11, which contained a salt of a fatty acid, had a considerably lower viscosity than the dispersions of Comparative Examples F and G which were produced in a comparable manner but in the absence a salt of a fatty acid. Moreover, Examples 8-11 illustrate that according to the present invention dispersions with a very high solids content and a very high HPMCAS content can be produced but which still have a low viscosity at 20° C.

The dispersions of Comparative Examples F and G and of Examples 8-11 were visually inspected and their mean particle size was measured after about 2 weeks. The dispersions of Comparative Examples F and G displayed agglomeration upon storage for about 2 weeks. In contrast thereto, the dispersions of Examples 8-11 did not display any agglomeration upon storage for about 2 weeks over the entire utilized range of sodium stearate as a surfactant.

Example 12

Example 1 was repeated, except that a Drais DCP-12 Advantis media mill (1.0 mm Ytterum Stabilized Zirconia media, 0.5 mm screen size) was used. The mill speed was initially set at 1600 rpm and then reduced as necessary down to about 1400 rpm to control the mill outlet temperature. Additionally ethylcellulose was added during grinding that comprised 48.0-49.5 wt. % ethyl groups and had a viscosity of 18-22 mPa·s, measured as a 5% solution in 80% toluene and 20 ethanol at 25° C. in an Ubbelohde viscometer. The ethylcellulose is commercially available from The Dow Chemical Company as Ethocel Std. 20. It was used as a film forming aid. The resulting dispersion comprised 19.1 percent and 6.4 percent ethylcellulose, based on the total weight of the dispersion.

The results in Table 1 below illustrate that a HPMCAS dispersion of fine particle size and sufficiently low viscosity at 20° C. is also achieved when the dispersion additionally comprises a film-forming aid, such as ethylcellulose.

Example 13

Example 1 was repeated, except that a Drais DCP-12 Advantis media mill (1.0 mm Ytterum Stabilized Zirconia media, 0.5 mm screen size) was used and an alkali metal oleate was used as a surfactant. The mill speed was initially set at 1600 rpm and then reduced as necessary down to about 1400 rpm to control the mill outlet temperature.

TABLE 1

| Example | Surfactant | HPMCAS, based on total [%] | surfactant, based on total [%] | surfactant, based on polymer[2] [%] | Mean (μm) | d50 (μm) | d90 (μm) | Viscosity at 20° C. [mPa*s] | Phase Transition temp. [° C.] | Standard deviation baseline viscosity | Stability after about 2 weeks | Mean after about 2 weeks (μm) |
|---|---|---|---|---|---|---|---|---|---|---|---|---|
| A | — | 20.4 | 0.00 | 0.0 | 3.6 | 3.2 | 6.7 | 5080 | <15 | 34 | Aggl. | 44.8 |
| B | Tween 80 | 20.0 | 1.12 | 5.6 | 32.4 | 4.5 | 108.1 | 2890 | <15 | 34 | Aggl. | 91.5 |
| C [1] | Sodium Dodecyl Sulfate | | | 4.8 | NA | NA | NA | NA | NA | NA | NA | NA |
| D | Sodium Dodecyl Sulfate | 24.2 | 0.17 | 0.7 | 1.9 | 1.4 | 3.9 | 112 | 19.0 | 1 | Aggl. | 6.5 |
| E | Pluronic L-44 | 20.8 | 1.00 | 4.8 | 1.9 | 1.4 | 3.9 | 3140 | <15 | 47 | Increased particle size | 57.9 |
| 1 | Sodium Stearate | 19.8 | 0.87 | 4.4 | 1.3 | 0.9 | 2.9 | 808 | 24.0 | 6 | No Aggl. | 2.3 |
| 2 | Sodium Stearate | 20.4 | 0.39 | 1.9 | 2.3 | 1.7 | 5 | 97 | 20.6 | 7 | — | — |
| 3 | Calcium Stearate | 24.3 | 0.61 | 2.5 | 1.4 | 0.8 | 3.2 | 75 | 26.4 | 3 | — | — |
| 4 | Potassium Stearate | 25.0 | 1.25 | 5.0 | 2.4 | 1.2 | 4.7 | 130 | 35.4 | 1 | No Aggl. | 1.7 |
| 5 | Potassium Stearate | 20.3 | 0.49 | 2.4 | 2.1 | 1.6 | 4.6 | 746 | 25.6 | 1 | Aggl. | 17.9 |
| 6 | Sodium Oleate | 29.1 | 0.99 | 3.4 | 1.9 | 1.4 | 4.1 | 146 | 33.8 | 1 | No Aggl. | 3.0 |
| F | — | 20.5 | 0.00 | 0.0 | 2.1 | 1.6 | 4.5 | 683 | <15 | 25 | Aggl. | 29.3 |
| G | — | 20.1 | 0.00 | 0.0 | 4.2 | 3.6 | 8.3 | 420 | <15 | 35 | Aggl. | 10.5 |
| 7 | Sodium Stearate | 18.5 | 0.92 | 5.0 | 3.2 | 2.2 | 8.9 | 118 | 29.7 | 2 | — | — |
| 8 | Sodium Stearate | 28.6 | 1.27 | 4.4 | 2.0 | 1.3 | 4.2 | 243 | 28.4 | 1 | No Aggl. | 1.6 |

TABLE 1-continued

| Example | Surfactant | HPMCAS, based on total [%] | surfactant, based on total [%] | surfactant, based on polymer[2] [%] | Mean (μm) | d50 (μm) | d90 (μm) | Viscosity at 20° C. [mPa*s] | Phase Transition temp. [° C.] | Standard deviation baseline viscosity | Stability after about 2 weeks | Mean after about 2 weeks (μm) |
|---------|-----------|------|------|------|-----|-----|-----|-----|------|---|----------|-----|
| 9 | Sodium Stearate | 27.6 | 1.05 | 3.8 | 2 | 1.4 | 4.4 | 108 | 34.6 | 1 | No Aggl. | 2.0 |
| 10 | Sodium Stearate | 29.2 | 0.58 | 2.0 | 2.2 | 1.7 | 4.8 | 38 | 28.9 | 1 | No Aggl. | 2.2 |
| 11 | Sodium Stearate | 30.2 | 0.60 | 2.0 | 1.8 | 1.4 | 3.8 | 54 | 28.1 | 2 | No Aggl. | 1.8 |
| 12 | Sodium Stearate | 19.1 | 0.48 | 1.9 | 1.5 | 1.1 | 3.5 | 252 | 24.0 | 4 | No Aggl. | 2.1 |
| 13 | Sodium Oleate | 29.1 | 0.73 | 2.5 | 2.7 | 2 | 5.5 | 78 | 28.9 | 1 | No Aggl. | 4.4 |

NA: not assessed
[1] viscosity too high, the mill was inoperable
Aggl: Agglomeration;
No Aggl: No Agglomeration
[2] polymer weight was HPMCAS weight, except in Example 13, where polymer weight was total of HPMCAS and ethylcellulose weight FIG. 1 illustrates the viscosity of the HPMCAS dispersions of Example 1 and of Comparative Examples A, B, D and E depending on its temperature. The freshly prepared HPMCAS dispersions of Example 1 and of Comparative Example D had a sufficiently low viscosity at 20° C. to be conveniently handled but an increased viscosity to adhere to the surface of a substrate (e.g. tablet or steel pin). However, the HPMCAS dispersion of Example 1 was stable upon storage for about 2 weeks; whereas the dispersion of Comparative Example D showed some agglomeration upon storage for about 2 weeks. Handling of the dispersion of Comparative Examples A, B and E at 20° C. was more difficult due to their higher viscosity. Moreover, the dispersion of Comparative Examples A, B and E showed agglomeration upon storage for about 2 weeks.

Example 14

Figure 2:
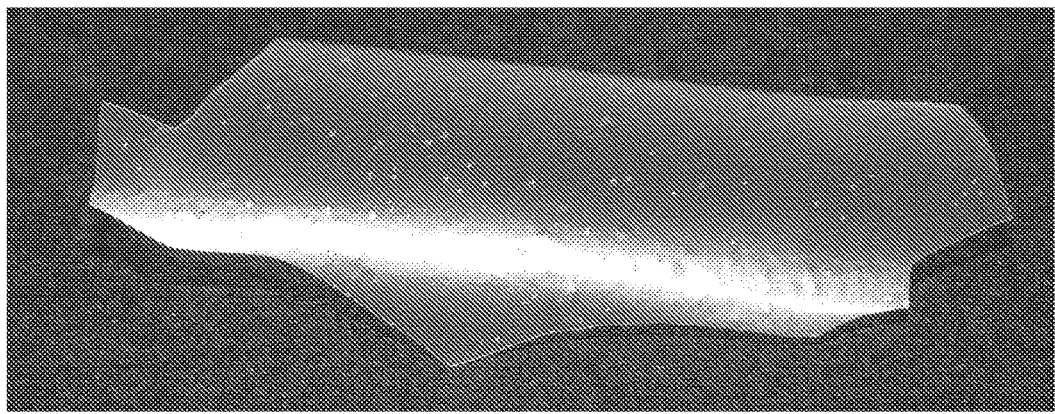
FIG. 2 is a photographical representation of a film cast from an aqueous composition of the present invention.

The dispersion prepared in Example 11 was used to evaluate film formation. The dispersion was stored at room temperature. For casting a film the dispersion was cooled to 12-16° C. while stirring the dispersion applying a moderate shear. 10% triethyl citrate (TEC) relative to HPMCAS was added drop wise to the dispersion. The TEC addition decreased the phase transition temperature of the dispersion. The resulting solids content of the dispersion was 33.8% (30.2% HPMCAS, 0.6% sodium stearate and 3.1% TEC). Stirring under moderate shear continued for additional 15-30 min at 12-16° C. Then the film was cast at room temperature on a steel plate using a casting device with a 400 μm gap. A free standing film was formed at room temperature. The wet film had a thickness of 400 micrometers; upon drying at 40° C. a film thickness of about 100 micrometers resulted and a residual moisture content of 2.6%. FIG. 2 represents a photograph of the cast film.

Example 15

Figure 3:
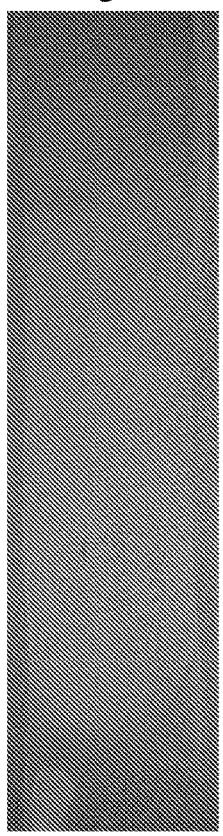
FIG. 3 is a photographical representation of another film cast from an aqueous composition of the present invention.

A dispersion comprising 2 wt.-% of sodium stearate as a surfactant was prepared as described in Example 10. The dispersion was stored at room temperature. For casting a film the dispersion was cooled to 10-15° C. while stirring the dispersion for 5 min. at 200 rpm. A mixture of 8.3% triethyl citrate (TEC), 8.3% dibutyl sebacate (DBS) and 1.1% of a poloxamer (plasticizer composition), based on the weight of HPMCAS, was added drop wise to the dispersion. The poloxamer was Pluronic L121, which is a poly(ethylene oxide) (PEO)-poly(propylene oxide) (PPO)-poly(ethylene oxide) (PEO) triblock copolymer of the structure $PEO_5$-$PPO_{68}$-$PEO_5$ and is commercially available from BASF Corporation. The resulting solids content of the dispersion was 33.3% (27.8% HPMCAS, 0.6% sodium stearate, 2.3% TEC, 2.3% DBS and 0.3% of Pluronic L121). Stirring under moderate shear continued at 10-15° C. for about 15-30 min. and at 12-18° C. for about another 15 min. Then the film was cast on a non-sticking plate using a casting device with a 380 μm gap. The wet film had a thickness of 380 micrometers. Upon drying at about 75° C. a film thickness of about 125 micrometers resulted. A free standing film having a smooth surface was formed. FIG. 3 represents a photograph of the cast film.

The invention claimed is:
1. An aqueous composition consisting of:
   a) at least 15 weight percent, based on the total weight of the aqueous composition, of dispersed hydroxypropyl methyl cellulose acetate succinate,
   b) from 0.05 to 5.0 percent of at least one salt of a fatty acid, based on the weight of the dispersed hydroxypropyl methyl cellulose acetate succinate,
   c) optionally one or more ingredient selected from the group consisting of fertilizers, herbicides, pesticides, vitamins, herbals and mineral supplements, drugs, plasticizers, film forming aids, coloring agents, pigments, opacifiers, flavors, taste improvers and antioxidants, and
   d) an aqueous diluent,
   wherein the median particle size, d50, of the dispersed hydroxypropyl methyl cellulose acetate succinate particles is up to 3 micrometers, such median particle size (d50) being the size at which 50 mass percent of the particles have a smaller equivalent diameter and 50 mass percent have a larger equivalent diameter, and wherein said composition has a viscosity between 20 mPa·s and 1000 mPa·s at 20° C.
2. The aqueous composition of claim 1 comprising from 0.5 to 5 percent of an ammonium, alkali metal or alkaline earth metal salt of a saturated or unsaturated fatty acid, based on the weight of the dispersed hydroxypropyl methyl cellulose acetate succinate.
3. The aqueous composition of claim 1 wherein the salt of a fatty acid is an ammonium, alkali metal or alkaline earth metal salt of stearic acid or oleic acid.

4. The aqueous composition of claim 1 comprising two or three plasticizers selected from i) citric esters, ii) esters of dicarboxylic acids, and iii) acetoglycerides or block copolymers comprising blocks of poly(ethylene oxide) and poly(propylene oxide), provided that two or three plasticizers are selected from different groups i)-iii).

5. The aqueous composition of claim 1 wherein the median particle size, d50, is up to 2 micrometers, such median particle size (d50) being the size at which 50 mass percent of the particles have a smaller equivalent diameter and 50 mass percent have a larger equivalent diameter.

6. The aqueous composition of claim 1 wherein d90 of the dispersed hydroxypropyl methyl cellulose acetate succinate particles is up to 9 micrometers, d90 being the diameter where 90 mass percent of the particles have a smaller equivalent diameter and the other 10 mass percent have a larger equivalent diameter.

7. The aqueous composition of claim 1 comprising
a) at least 20 weight percent, based on the total weight of the aqueous composition, of dispersed hydroxypropyl methyl cellulose acetate succinate particles having a median particle size, d50, of up to 3 micrometers and a d90 of up to 9 micrometers and
b) from 1.0 to 5.0 percent of an alkali metal salt of stearic acid or oleic acid, based on the weight of the dispersed hydroxypropyl methyl cellulose acetate succinate.

8. The aqueous composition of claim 1 comprising at least 20 weight percent of said hydroxypropyl methyl cellulose acetate succinate, based on the total weight of the aqueous composition.

9. The aqueous composition of claim 1 comprising at least 27.6 weight percent of said hydroxypropyl methyl cellulose acetate succinate, based on the total weight of the aqueous composition.

10. A process for producing the aqueous composition of claim 1 comprising the steps of
grinding, in the presence of an aqueous diluent, at least one hydroxypropyl methyl cellulose acetate succinate, and
blending from 0.05 to 5.0 percent of at least one salt of a fatty acid and optionally one or more adjuvants with the hydroxypropyl methyl cellulose acetate succinate before, during or after the grinding of the hydroxypropyl methyl cellulose acetate succinate, the percentage of the fatty acid salt being based on the weight of the hydroxypropyl methyl cellulose acetate succinate.

11. A process for producing the aqueous composition of claim 1 comprising the steps of:
melting a hydroxypropyl methyl cellulose acetate succinate;
emulsifying the molten hydroxypropyl methyl cellulose acetate succinate in an aqueous diluent,
adding from 0.05 to 5.0 percent of a salt of a fatty acid, based on the weight of the dispersed hydroxypropyl methyl cellulose acetate succinate, and optionally one or more adjuvants before, during or after the step of emulsifying the molten hydroxypropyl methyl cellulose acetate succinate in the aqueous diluent, and
cooling the emulsion to form an aqueous dispersion.

12. A dosage form being coated with a coating prepared from the aqueous composition of claim 1.

13. A capsule shell made from the aqueous composition of claim 1.

14. A process for producing capsule shells comprising the steps of providing the aqueous composition of claim 1,
pre-heating molding pins to a temperature higher than the aqueous composition,
dipping the pre-heated molding pins into the aqueous composition,
forming a film on said molding pins by withdrawing said pins from said aqueous composition, and
drying the film on the molding pins.

* * * * *